United States Patent [19]

Franke

[11] Patent Number: 5,094,517
[45] Date of Patent: Mar. 10, 1992

[54] POLYIMIDE WAVEGUIDES AS OPTICAL SENSORS

[75] Inventor: Hilmar Franke, Bramsche, Fed. Rep. of Germany

[73] Assignee: Hoechst Aktiengesellschaft, Frankfurt am Main, Fed. Rep. of Germany

[21] Appl. No.: 565,503

[22] Filed: Aug. 10, 1990

[30] Foreign Application Priority Data

Aug. 11, 1989 [DE] Fed. Rep. of Germany ....... 3926604

[51] Int. Cl.⁵ .............................................. G02B 6/10
[52] U.S. Cl. ...................................... 385/12; 385/141
[58] Field of Search ......................... 350/96.10–96.14

[56] References Cited

U.S. PATENT DOCUMENTS 4,274,709  6/1981  Asai .................................... 385/141

FOREIGN PATENT DOCUMENTS

WO89/07756  8/1989  PCT Int'l Appl. .

OTHER PUBLICATIONS

"Protective Coatings on Cylindrical Waveguides made by the Double-Crucible Technique from Multi Component Glasses" by Kucharaski, Szkio Ceram, 36(1) 10–14 year 1985.

Appln. Phys. Letter, vol. 52, No. 10, R. Reuter and H. Franke, Monitoring Humidity by Polyimide Lightguides, Mar. 7, 1988, pp. 778–779.

IBM Technical Disclosure Bulletin, vol. 32, No. 4A, Method of Measuring Vapor Concentration, Sep. 1989, pp. 468–469.

*Primary Examiner*—Akim Ullah

[57]  ABSTRACT

The invention relates to a polyimide waveguide which is used as an optical sensor for the quantitative determination of liquids in the vapor phase, as well as for the determination of $NH_3$, "$NH_4OH$", $NO_2$ and $N_2O_5$. The polyimide waveguide is composed of a cover layer, one or two layers of a polyamide-imide or a perfluorinated polyimide and a substrate.

17 Claims, 5 Drawing Sheets

THREE LAYER WAVEGUIDE

FOUR LAYER WAVEGUIDE

POLYIMIDE WAVEGUIDES AS OPTICAL SENSORS

The invention relates to a polyimide waveguide as an optical sensor which is used for the quantitative detection of liquids in the vapor phase, particularly, polar liquids in the vapor phase and for the detection of $NH_3$, "$NH_4OH$", $NO_2$ and $N_2O_5$.

Polyimides are used as material for waveguides and in optoelectronics as coatings and fillings for electronic embedding material. This utility of polyimides arises despite their sensitivity to "humidity" due to interactions of the vapor phase of the liquid components in the vicinity of the surface of the polyimide. Humidity measurements are usually obtained by two methods. For example, in the hair hygrometer method, the dependence of the length of a hair or textile fiber upon humidity is determined by means of specially prepared hairs and textile fibers, inter alia. Another method, the capacitive process utilizes a polymer film wherein the "humidity" is measured by an altered capacitance (cf. product description of an instrument for indicating moisture and temperature, model HMI 32 from the company Driesen + Kern, Tangstedt).

Furthermore, polyimide waveguides are known as sensors using uncured polyimide films for the qualitative determination of water (cf. Appl. Phys. Lett. 52 (10), 1988). However, these devices do not permit any quantitative detection of water and other liquids.

There accordingly existed a need to provide a measuring arrangement for the quantitative determination of "humidity", i.e., the water content of air and content of specific molecules in the vapor phase of a liquid containing those molecules.

Surprisingly, it has been found that molecules of liquids in the vapor phase, particularly polar molecules in the vapor phase, participate in optically anisotropic interactions with polyimide surfaces and that the interactions can be detected and quantitatively measured optically. The optical sensors of the invention may also be utilized repeatedly.

It was possible to achieve this objective by the production of a polyimide waveguide which operates as an optical sensor and has several advantages when compared with the known methods of measurement.

The measurement process has the following features:
a) detection and measurement is accomplished optically;
b) the detected signals can be displayed digitally;
c) the process is a comparative measurement of the phase difference of two polarizations and is thus independent of fluctuations of the absolute value thereby enabling an accurate measurement of the phase difference;
d) the sensor can operate also in a vacuum as well as under variable pressure conditions;
e) the process operates for liquids, particularly polar liquids, in the vapor phase; and
f) the process can separately distinguish water from other liquids.

The invention relates to a polyimide waveguide which comprises at least one layer of a polyamide-imide or perfluorinated polyimide and a method for the detection of humidity using the waveguide.

The object of the invention is to use the polyimide waveguide as an optical sensor for the detection of liquids in the vapor phase.

A further object of the invention is to use the polyimide waveguide as an optical sensor for the detection of $NH_3$, "$NH_4OH$", $NO_2$ and $N_2O_5$.

A further object of the invention is to use structured polyimide waveguides in the shape of strip waveguides, interferometer structures or directional coupler structures as optical sensors for the detection of liquids in the vapor phase.

Polyimide waveguides comprise polyamide-imides and perfluorinated polyimides (referred to as "polyimide(s)"), for example, HFDA-ODA, HFDA-HFDAM-33, HFDA-HFDAM-44 or combinations of HFDA-HFDAM-33 and HFDA-HFDAM-44. The meaning of these abbreviations are as follows:

HFDA: hexafluoro-iso-propylidene-2,2'-di-(phthalic anhydride)
ODA: oxydianiline
HFDAM-33: hexafluoro-iso-propylidene-2,2'-di(3-aminobenzene) and
HFDAM-44: hexafluoro-iso-propylidene-2,2'-di (4-aminobenzene).

The polyimides utilized by this invention have the following structural formulae:

HFDA-ODA

HFDA-HFDAM-33

HFDA-HFDAM-44 wherein n is an integer from 50,000 to 100,000 for HFDA-ODA, an integer from 50,000 to 80,000 for HFDA-HFDAM-33, and an integer from 50,000 to 100,000 for HFDA-HFDAM-44.

The particularly preferred waveguides include HFDA-ODA or a combination of HFDA-HFDAM-33 and HFDA-HFDAM-44.

The polyimide waveguides are structured so that the TM and TE modes of polarized light are coupled into the polyimide layer (or layers) in phase. TM refers to the transversal magnetic polarization and TE refers to the transversal electric polarization. The TM polarization is that polarization for which the electric field "E" vector of the electromagnetic wave oscillates perpendicularly to the polyimide film surface. The TE polarization is that polarization for which the electric field "E" vector of the electromagnetic wave oscillates parallel to the polyimide film surface. An atmosphere on the surface of the polyimide layer optically interacts with the in phase TM and TE modes causing a phase disturbance (birefringence alteration) which can be optically measured to identify and quantify molecules of a liquid vapor in the atmosphere.

The polyimide waveguide produced for the measurement of "humidity" can be arranged using at least three or four layers as follows:

Cover layer (containing the atmosphere being analyzed)/polyimide layer/substrate for a three-layered waveguide; and Cover layer/polyimide layer/polyimide layer/substrate for a four-layered waveguide.

Preferably, a four-layer waveguide is used. Additional layers of the polyamide may be added to form a waveguide having additional layers.

For both the three and four layer arrangements of the polyimide waveguide, the "atmosphere", which contains the vapor phase, serves as the cover layer and the substrate is preferably glass. However, the substrate may be any substance that is transparent and has a refractive index lower than that of the polyimide layer.

Waveguides having three layers preferably comprise a layer of HFDA-ODA, whereas waveguides having four layers preferably include a layer each of HFDA-HFDAM-33 and HFDA-HFDAM-44.

HFDA-HFDAM-33 and HFDA-HFDAM-44 can be fully cured and utilized in good and stable waveguides.

By using two layers including HFDA-HFDAM-33 and HFDA-HFDAM-44 as waveguides, it is possible to obtain up to a ten-fold increase in the sensitivity of the measurement.

One example of the four layer waveguide is composed of the following arrangement of layers:

Cover layer/an upper layer of HFDA-HFDAM-33 (referred to as "33")/a lower layer of HFDA-HFDAM-44 (referred to as "44")/substrate. The refractive indices "n" will have the following parameters:

$n_{TE}$(upper layer) approximately or about equal to $n_{TE}$(lower layer); and $n_{TM}$(upper layer) greater than $n_{TM}$(lower layer).

In this case, $n_{TE}(33) = 1.543$, $n_{TE}(44) = 1.541$, $n_{TM}(33) = 1.538$ and $n_{TM}(44) = 1.516$;

where $n_{TE}$ is the refractive index for the TE polarization and $n_{TM}$ is that for the TM polarization. The layers (33 and 44) used to form the waveguide are distinguishable with respect to the TM polarization in that the lower layer (44) due to its lower $n_{TM}$ does not transmit the TM mode. Rather, the TM mode is only transmitted through the upper layer (33). However, since the $n_{TE}$ of both layers are about equal, the TE mode is transmitted through both layers of polyimide. In view of the shorter distance traveled by the TM mode through only the upper layer, the TM mode light intensity at the polyimide surface is increased, thereby increasing the anisotropic interaction with the atmosphere and amplifying its phase shift when compared to the TE mode, which travels a longer distance through both layers and correspondingly has a less intense interaction with the atmosphere. In this way, the phase disturbance for the TM polarization at the surface is increased, leading to an increase in sensitivity (see FIG. 7) of the device.

Using the optical sensor according to the invention, it is possible to detect and measure liquids in the vapor phase, for example water, $C_1-C_3$ alcohols, gasoline, light heating fuel oil and $C_1-C_3$ carboxylic acids. In addition, it is possible to detect and measure $NH_3$, $NH_4OH$, $NO_2$ and $N_2O_5$. It is preferred to use the optical sensor to detect water and $C_1-C_3$ alcohols or mixtures thereof. It is also preferred that the sensor be utilized to detect a single type of molecule or a mixture of two types of molecules.

Polyimide waveguides can also be used as optical sensors for detection of liquids, in shapes such as strip waveguides, interferometer structures or directional coupler structures.

The optical sensor may also be used to detect other physical properties (e.g., local pressure, temperature and electric fields) which influence the equilibrium between the polyimide surface and the humid atmosphere. An example of this is observed when, for constant humidity, the absorption/desorption equilibrium will change when infrared or microwave radiation is absorbed by the polyimide film. This absorption of radiation causes an increase in the local temperature which leads to a different local relative humidity at the surface. Changes in the relative humidity at the polyimide surface can be detected and measured by the present invention.

The ability to use the polyimide waveguide as an optical sensor is derived from the interaction of molecules with the polar imide groups within the polyimide backbone. Each type of molecule in the vapor phase is related to a time constant in that each molecule is absorbed and desorbed by the polyimide waveguide over different time intervals and therefore can be distinguished in a vapor phase mixture. The intensity of the obtained anisotropy (birefringence alteration) corresponds to the concentration of that particular molecule in the vapor phase atmosphere.

Figure 1:
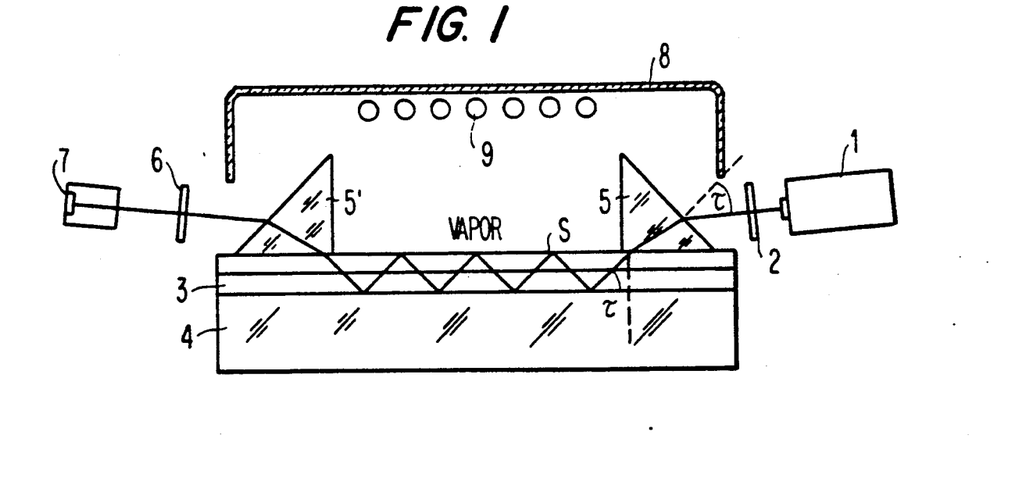
FIG. 1 shows an apparatus used for measuring polar molecules in the vapor phase of a liquid in accordance with the present invention.

In order to determine "humidity", one embodiment which may be used is the apparatus shown in FIG. 1. The light of He-Ne laser (1) passes through half-wave plate (2), which polarizes the light at 45° (such that the TE and TM modes are equal) and rotates the TE and TM the polarization modes, at a particular angle of incidence, $\tau$, onto a polyimide waveguide which is composed of a substrate (4) coated with a polyimide film (3). The substrate is a substance which has a refractive index which is lower than that of the polyimides so the light is reflected up into the polyimide. Glass is a suitable substrate. 90° prisms made of heavy flint glass (5) are used to adjust the angle of incidence of the laser beam and to couple the TM and TE modes into and out of the waveguide. The TM and TE modes coupled into the polyimide film (3), which may typically have a length of several centimeters, preferably, about 2 cm., is reflected to the surface (S) of the film where it contacts the vapor of the liquid and there is an optical anisotropic interaction which shifts the phase of the TM and TE modes. The TM and TE modes are coupled out of the film (3) by heavy flint glass prism (5') and pass through an analyzer (6) which detects the alteration of the TM and TE modes. The analyzer (6) may be set at an angle of 90° to the direction of polarization so it can detect disturbances of the phase of the TM and TE modes. The detector (7) receives the signal of disturbance from the analyzer (6) and measures absolute intensity of the phase change, called the birefringence alteration, and converts the optical signal to an electrical signal which can then be displayed by any known means.

The apparatus may be enclosed with a glass bell (8), which contains silica gel (9) in order to reduce the humidity in the apparatus which is due to the atmospheric humidity to illustrate the sensitivity of the device to changes in humidity.

In order to obtain the desired results, the moisture sensor (FIG. 1) should transmit a particular TE mode (e.g., $TE_5$) and a matched TM mode (e.g., $TM_6$) polarization simultaneously. Specific polarization modes, for example $TE_5$ and $TM_6$, can be selected for transmittal through the waveguide by adjusting the angles of incidence $\tau$.

The moisture sensor is constructed by utilizing the theoretical curves (FIG. 2) computed from the substantive refractive index parameters for TE and TM. In this case, FIG. 2 plots these curves for HFDA-ODA.

Figure 2:
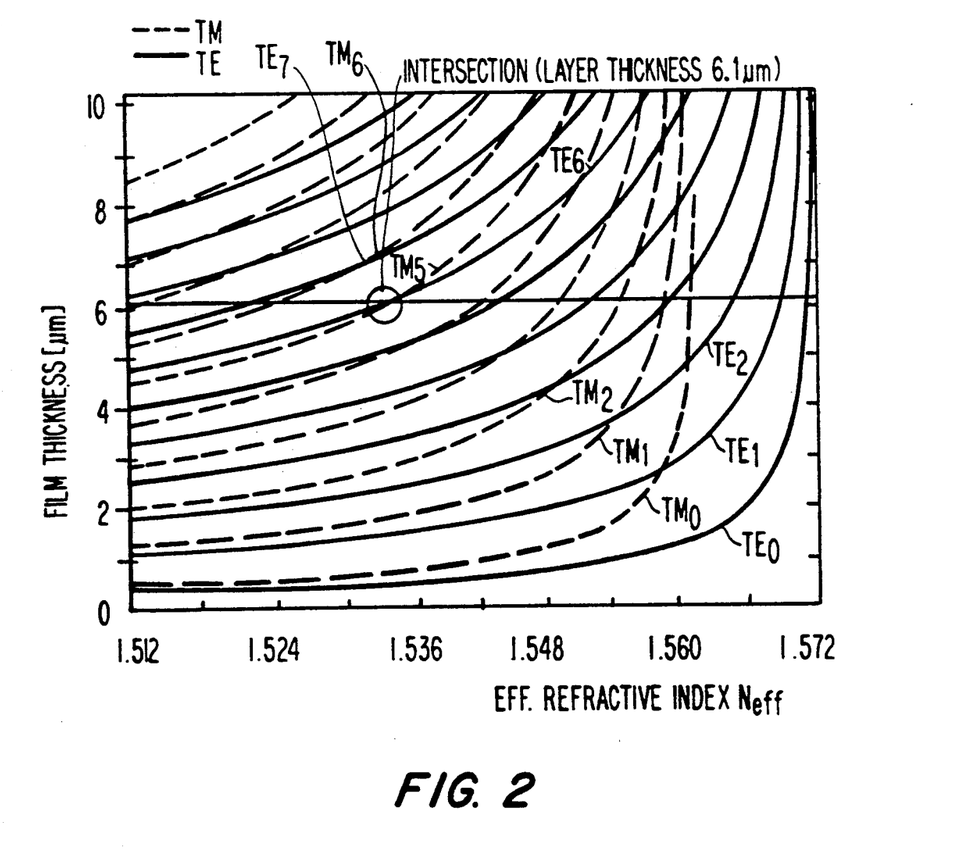
FIG. 2 is a plot of film thickness ($\mu$m) versus effective refractive index ($N_{eff}$) for determining at what film thickness of HFDA-ODA the mode matching for the TE and TM polarizations may be obtained.

The curves shown in FIG. 2 plot the film thickness of the waveguide [$\mu$m] against the effective refractive index $N_{eff}$ of the appropriate TE and TM modes. These families of curves for the TE and TM polarizations, represent the resonance conditions which arise from the transverse resonance condition (TRC) for plane waveguides. In order to transmit the TE and TM modes through the polyimide film (3) so that they are in phase, the TE and TM modes must be matched for a particular film thickness. The desired property of matching of modes exists at a point of intersection of the TM and TE curves. For instance, the point of intersection indicated in FIG. 2 corresponds to the matched modes for $TE_5$ and $TM_6$ at a film thickness of 6.1 $\mu$m for HFDA-ODA. It is desirable to have matched modes and thereby transmit the TE and TM modes in phase in order to measure the birefringence alteration (or phase shifting) caused by the anisotropic interaction between the waveguide and the molecules in the vapor phase of the liquid at the waveguide surface (S) as the TM and TE modes pass through the polyimide film.

Figure 3:
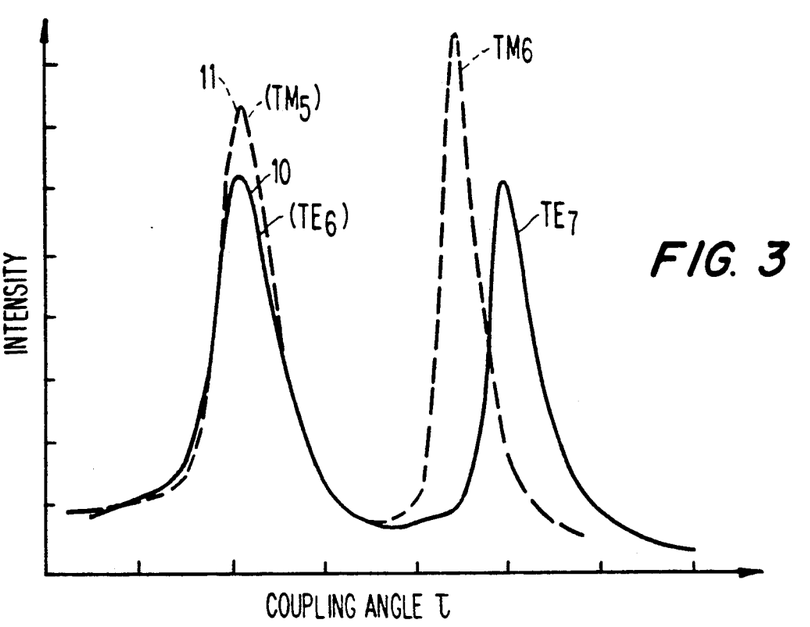
FIG. 3 is a plot of intensity versus coupling-in angle ($\tau$) depicting the TE/TM intersection point determined from the graph in FIG. 2.

FIG. 3 depicts the intensity of the optical signal for modes $TM_5$ and $TE_6$, and $TM_6$ and $TE_7$, plotted against the coupling-in angle $\tau$, for an extract of the measured mode spectrum (FIG. 2) of an anisotropic polyimide film HFDA-ODA having a layer thickness of 6.1 $\mu$m. It is at this film thickness as shown in FIG. 2 that the $TM_5$ and $TE_6$ modes will be matched. The representation shows the $TE_6$ mode (10) and the $TM_5$ mode (11) which can be coupled at the same angle of incidence. The two modes overlap to such an extent that there will be sufficient overlapping of the matched modes even after the anisotropic interactions force the modes out of phase. The intensity is therefore still strong enough to be measured. The figure also shows that the $TE_7$ and $TM_6$ modes are out of phase, and therefore not matched, for the HFDA polyimide having a thickness of 6.1 $\mu$m. The period of time represented in FIG. 3 is the initial state (of the vapor phase) before measuring the birefringence alteration.

The overlapping of the TE and TM modes shown in FIG. 3 is undertaken experimentally by preparing a waveguide having the thickness selected from the point of intersection in FIG. 2. The film thickness is obtained by selecting a specific centrifuging speed of rotation on the photoresist centrifuge employed for producing a film from a polyimide solution.

EXAMPLES

Example 1

Forming a calibration curve for the material HFDA-ODA

Figure 4:
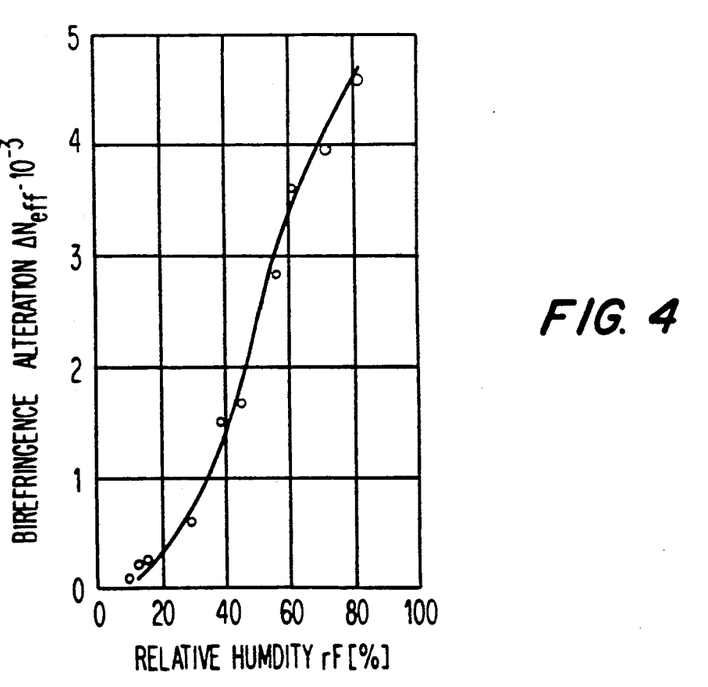
FIG. 4 is a calibration curve representing the birefringence alteration ($\Delta N_{eff}.10^{-3}$) and its correspondence to air humidity using HFDA-ODA for the polyimide waveguide material.

In FIG. 4 a calibration curve has been plotted which represents the birefringence alteration $\Delta N_{eff} \cdot 10^{-3}$ at equilibrium for the material HFDA-ODA, $\Delta N_{eff} = N_{TE6} - N_{TM5}$, and has been plotted against the relative humidity RH [%] for moisture in the air. The anisotropy measurement was obtained for the entire range from 0 to 100% humidity. This calibration curve is dependent upon which polyimide waveguide and polar molecules are utilized.

Example 2

Evacuation and ventilation of a container with moist air

Figure 5:
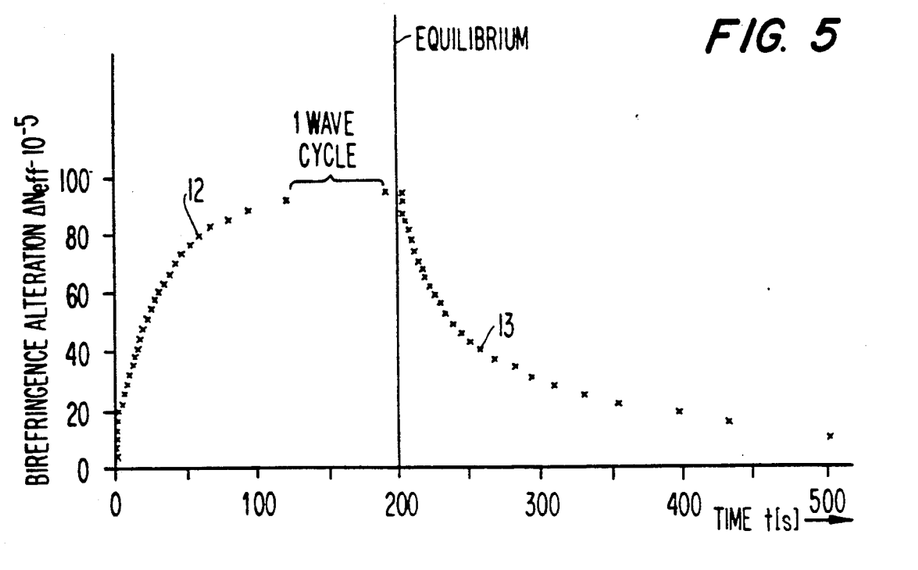
FIG. 5 is a plot of the time dependance of the measured birefringence alteration, $\Delta N_{eff}$, for water on an HFDA-ODA waveguide.

A multiplicity of intensity fluctuations was observed during the evacuation of a test vessel. When these fluctuations were evaluated, it was then possible to represent the pertinent optical birefringence alteration $\Delta N_{eff}$ as a function of the time [s]. FIG. 5 shows this fluctuation for the absorption, first period (12) (before equilibrium is reached) and the desorption, second period (13) (after equilibrium has been reached) of water on an HFDA-ODA waveguide. Equilibrium is the state at which absorption and desorption are at equilibrium or equal. Here $\Delta N_{eff}$ is the index difference which was obtained from the phase difference of the transmitted TE and TM polarization modes or the birefringence alteration. In each instance, it was possible to associate a reaction constant, which signifies the absorption speed, with the root-type curve.

Example 3

Sensitivity measurement of an alcohol/water mixture

The surrounding atmosphere of a four-layer waveguide composed of an HFDA-HFDAM-33/HFDA-HFDAM-44 double layer was enriched with a mixture of methanol and water, whereupon the sensor reacted in the first instance to water with a specified rate constant and then to the alcohol.

Figure 6:
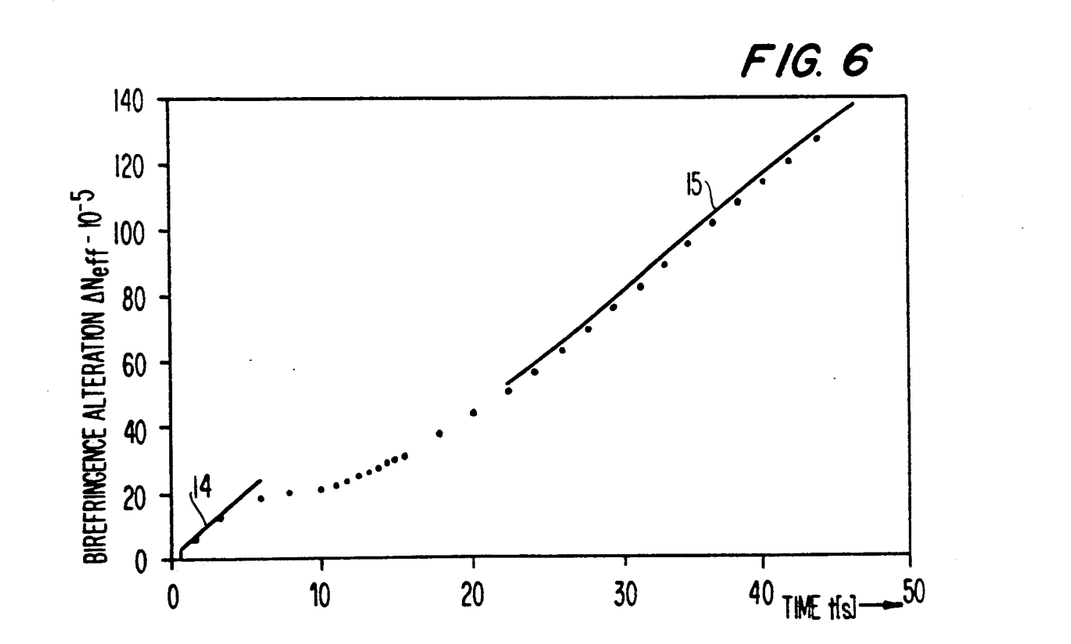
FIG. 6 is a plot of the anisotropic reaction, birefringence alteration $\Delta N_{eff}.10^{-5}$ versus time [s], of an HFDA-HFDAM-33 three-layer waveguide when enriched with a mixture of water and methanol.

This is further illustrated in FIG. 6, which depicts birefringence alteration $\Delta N_{eff} \cdot 10^{-5}$ plotted against the time [s] for a three-layer waveguide using HFDA-HFDAM-33. It was observed that the curve adopts a different curve for water (14) as compared with methanol (15). The sensor responds to methanol with a differential sensitivity ($\Delta N_{eff}/t$) which varies from its sensitivity to water, thereby enabling water to be separately distinguished from methanol. Time is indicated in seconds.

The curve for water (14) and the curve for methanol (15) are calculated using the known procedures for analyzing a diffusion process in which $\Delta N_{eff} = C\sqrt{dt}$ where C is a constant relating to the concentration of the molecule, d is the diffusion coefficient for a particular type of molecule and t is the time. The curve will be characteristic for each different molecule and will permit the identification of different molecules.

The concentration of the molecule can be obtained by comparing the birefringence alteration at equilibrium for the molecule in the mixture (such as in FIG. 6) with the corresponding birefringence alteration in the calibration curve for that molecule (such as in FIG. 4). The concentration of that molecule in the sample being analyzed can be read from the calibration curve.

By providing the detector (7) of FIG. 1 with a memory containing the data to produce calibration curves of the specific molecules to be analyzed and the capability to generate data for the birefringence alteration over time, the birefringence alteration at the equilibrium point for a particular molecule can be determined and a comparison with the calibration curve can be made to generate automatically the identity of the molecule and its concentration.

Example 4

Figure 7:
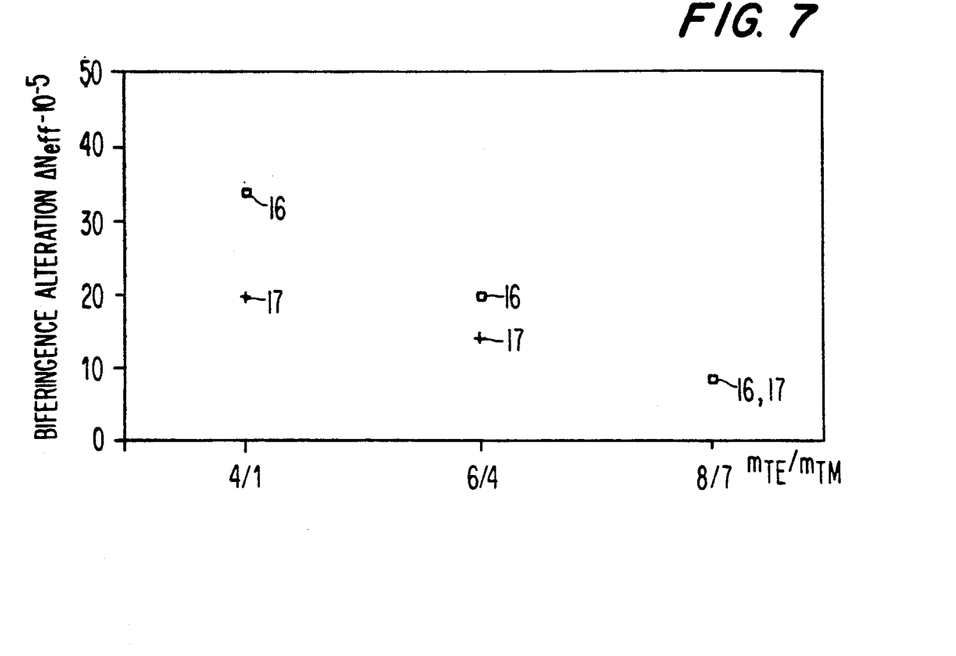
FIG. 7 is a plot of birefringence alteration $\Delta N_{eff}.10^{-5}$ versus various index matching modes, $m_{TE}/m_{TM}$, for a four-layer waveguide consisting of HFDA-HFDAM-33/HFDA-HFDAM-44 on glass illustrating the increased sensitivity obtained with certain matched modes.

FIG. 7 shows a plot of the birefringence alteration $\Delta N_{eff} \cdot 10^{-5}$ versus $m_{TE}/m_{TM}$, which is matched modes for TE and TM modes, at a relative air humidity of 42% (16) and in the evacuated condition (17) for an HFDA-HFDAM-33/HFDA-HFDAM-44 four-layer waveguide. The symbol, "m", represents the "mode order"-]with respect to TE and TM.

Accordingly, FIG. 7 shows the sensitivity of the sensor when differing mode matchings are employed. Measurements were made for 3 different mode matchings of TE and TM polarizations. The plotted $\Delta N_{eff}$ values correspond to humidity (moisture) in air of 42% in all three cases. It is clearly possible to discern the increase in the sensitivity of measurement when using the mode matching 4/1 as compared with the combinations for higher modes 6/4 and 8/7. 4/1 represents the phase matching for $m_{TE}=4$ and $m_{TM}=1$. In the case of this matching, a TM mode, that is $m_{TM}=1$, was used which is transmitted only in the upper HFDA-HFDAM-33 layer. The last mentioned mode can be designated as the "surface mode".

The expression "surface modes" is intended to refer to $m_{TM} \leq 2$ in which the modes exhibit at the surface an especially high intensity and thus a high evanescent field. These surface modes, $m_{TM}=0,1$ or 2, generally will be transmitted in the upper layer of the two polyimide layers meaning that the sensitivity of the waveguide can be increased. On the other hand, "space modes" show a high intensity in the interior of the film and only a weak evanescent field at the surface and $m_{TM} > 2$. The space modes $m_{TM}=2,3,4$, etc. generally will not have a high intensity at the surface and therefore will not be as sensitive in a four-layer waveguide. The space modes are transmitted through both layers of the polyimide.

Example 5

Sensitivity measurement for gasoline

Figure 8:
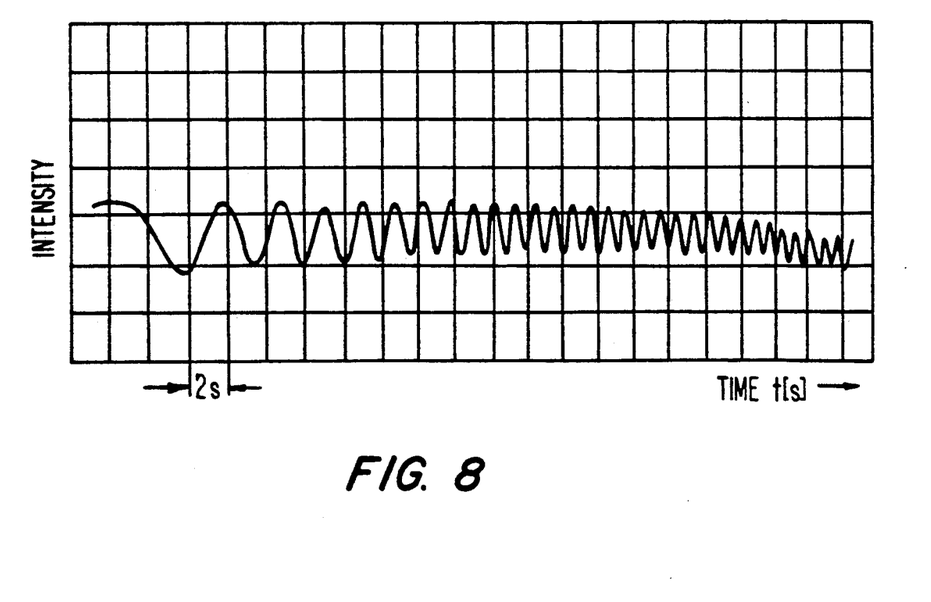
FIG. 8 is a plot of intensity versus time, depicting the sensitivity of the polyimide waveguide optical sensor to the presence of petroleum gasoline in the vapor phase.
Figure 9:
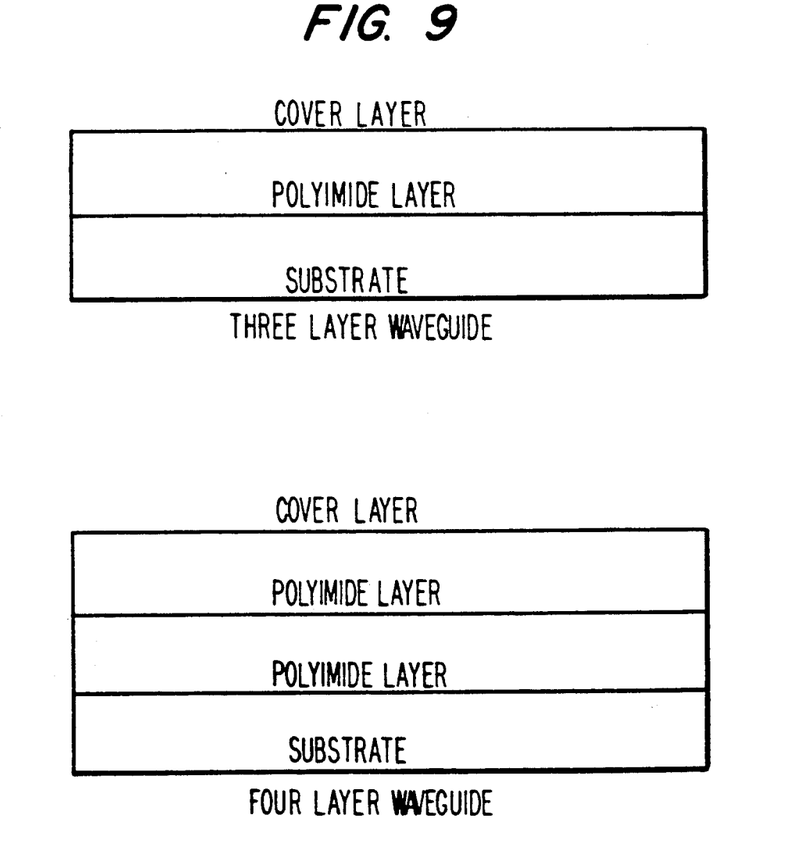
FIG. 9 depicts the structural arrangement for both three and four layer polyimide optical waveguides.

The container with the three-layer HFDA-HFDAM-33 optical polyimide sensor, was evacuated and subsequently connected to a storage vessel containing petroleum gasoline, so that the saturated vapor pressure at room temperature was established. FIG. 8 shows an extract of the measured cycles (i.e., the difference between the two maxima in the intensity curves of FIG. 3), from which the sensitivity of the sensor to petroleum gasoline can be seen. Time is indicated in two second intervals.

Example 6

Determination of ethanol vapors

The four-layer polyimide sensor described in Example 3 was surrounded with a closed container. The volume of air enclosed (20° C., 65% RH) was then enriched with ethanol vapor. In this case, it was possible to detect less than 3 $\mu l/m^3$ $C_2H_5OH$.

Example 7

Using the arrangement described in connection with Example 6, the sensitivity to propanol was determined. In this case, the sensitivity limit was at a level of 1 $ml/m^3$ $C_3H_7OH$.

I claim:

1. A polyimide waveguide consisting of at least two layers of a polyamideimide or perfluorinated polyimide coated onto a substrate and contacting a cover layer of liquid in the vapor phase at the surface of the polyamide-imide or perfluorinated polyimide.

2. The polyimide waveguide as claimed in claim 1, wherein the sequence of layers is said cover layer, an upper layer of HFDA-HDAM-33, a lower layer of HFDA-HFDAM-44, and said substrate, wherein HFDA-HFDAM-33 is hexafluoro-iso-propylidene-2,2'-di-(3-aminobenzene) and HFDA-HFDAM-44 is hexafluoro-iso-propylidene-2,2'-di (4-aminobenzene), and the cover layer and the substrate are glass.

3. An optical sensor for the determination of liquids in the vapor phase comprising a polyimide waveguide as claimed in claim 1.

4. The optical sensor as claimed in claim 3 wherein the liquids determined are selected from the group consisting of water, $C_1$-$C_3$ alcohols, gasoline, light heating fuel oil and $C_1$-$C_3$ carboxylic acids in the vapor phase.

5. An optical sensor for the determination of $NH_3$, "$NH_4OH$", $NO_2$ and $N_2O_5$ comprising a polyimide waveguide as claimed in claim 1.

6. The optical sensor for the determination of liquids in the vapor phase comprising a polyimide waveguide as claimed in claim 1 wherein said polyimide waveguide is selected from the group consisting of strip waveguides, interferometer structures and directional complex structures.

7. The optical sensor as claimed in claim 3 and further including means for the modulation or measurement of influences which have an effect on the equilibrium at the polyimide surface and the measurement space, such as pressure fluctuations, electric fields and microwaves.

8. The optical sensor as claimed in claim 5 and further including means for the modulation or measurement of influences which have an effect on the equilibrium at the polyimide surface and the measurement space, such as pressure fluctuations, electric fields and microwaves.

9. A polyimide waveguide as claimed in claim 1 in which the substrate is glass and the polyamide-imide or perfluorinated polyimide is HFDA-ODA, HFDAM-33, HFDA-HFDAM-44 or a combination of HFDA-HFDAM-33 and HFDA-HFDAM-44.

10. A device for detecting the presence of and measuring the relative amount of a molecule in a vapor comprising
    a polyimide waveguide consisting essentially of at least one layer of a polyamide-imide or perfluorinated polyimide coated onto a substrate; means for directing a polarized light onto the polyimide waveguide and coupling the polarized light into the layer of polyamide-imide or perfluorinated polyimide;
    an area adjacent the surface of the polyimide waveguide for receiving the vapor of the liquid so that the vapor is in contact with the polyamide-imide or perfluorinated polyimide layer;
    means for coupling the polarized light out of the polyimide waveguide, and
    means for measuring the intensity of the phase shift of the polarized light.

11. The device as claimed in claim 10 in which means for directing a polarized light includes means for directing TM and TE modes of said polarized light.

12. The device as claimed in claim 10 in which means for directing a polarized light includes means for directing TM and TE modes of said polarized light at an angle of about 45°.

13. The device as claimed in claim 12, in which the substrate has a refractive index which is lower than that of the polyamide-imide of perfluorinated polyimide.

14. The device as claimed in claim 11, in which the device has one or two layers of polyamide-imide or perfluorinated-polyimide.

15. The device as claimed in claim 13, in which the polyamide-imide or perfluorinated polyimide is selected from the groups consisting of HFDA-ODA, HFDA-HFDAM-33, HFDA-HFDAM-44 or combinations of HFDA-HFDAM-33 and HFDA-HDAM-44.

16. The device as claimed in claim 12 in which the device has two layers, an upper and lower layer, and $n_{TM}$ (upper layer) is greater than $n_{TM}$ (lower layer) and $n_{TE}$ (upper layer) is about equal to $n_{TE}$ (lower layer).

17. The method for detecting the presence of a vapor comprising
    directing and coupling a polarized light into the polyamide-imide or perfluorinated polyimide layer of a polyimide waveguide including a polyamide-imide or perfluorinated polyimide layer coated on a substrate;
    contacting the surface of the polyamide-imide or perfluorinated layer with a vapor to induce an anisotropic interaction to cause an optical phase shift of the polarized light in the polyimide waveguide; and
    measuring the intensity of the optical phase shift caused by the anisotropic interaction.

* * * * *